US008371181B2

(12) United States Patent
Wiederin

(10) Patent No.: US 8,371,181 B2
(45) Date of Patent: Feb. 12, 2013

(54) CONTINUOUS FLOW PUMP

(75) Inventor: Daniel R. Wiederin, Omaha, NE (US)

(73) Assignee: Elemental Scientific, Inc., Omaha, NE (US)

(*) Notice: Subject to any disclaimer, the term of this patent is extended or adjusted under 35 U.S.C. 154(b) by 516 days.

(21) Appl. No.: 12/643,369

(22) Filed: Dec. 21, 2009

(65) Prior Publication Data

US 2011/0146389 A1 Jun. 23, 2011

(51) Int. Cl.
*F04B 23/06* (2006.01)
*G01N 1/14* (2006.01)
*G01N 1/38* (2006.01)
*G01N 35/10* (2006.01)

(52) U.S. Cl. ........... 73/863.03; 73/64.56; 73/863.71; 73/864.17; 73/864.21; 73/864.22; 73/864.34; 73/864.35; 73/864.84; 73/864.87; 73/28.01; 417/62; 422/509; 422/539

(58) Field of Classification Search ............ 73/1.05, 73/28.01, 61.59, 64.56, 863.03, 863.71, 863.73, 73/864, 864.17, 864.21–864.22, 864.34–864.35, 73/864.84, 864.87; 250/288; 417/62; 422/81–82, 422/509, 538–540
See application file for complete search history.

(56) References Cited

U.S. PATENT DOCUMENTS

| | | | |
|---|---|---|---|
| 4,076,420 A * | 2/1978 | De Maeyer et al. ............ 356/73 |
| 4,528,161 A * | 7/1985 | Eckert ............................. 422/509 |
| 4,968,485 A * | 11/1990 | Morita .......................... 422/509 |
| 5,297,431 A * | 3/1994 | White ......................... 73/864.22 |
| 5,449,902 A * | 9/1995 | Onishi et al. .................. 250/288 |
| 6,315,952 B1 * | 11/2001 | Sklar et al. ................... 422/81 X |
| 6,324,924 B1 * | 12/2001 | Peterson ......................... 73/864 |
| 7,157,051 B2 * | 1/2007 | King et al. ................... 422/81 X |
| 2002/0192113 A1 * | 12/2002 | Uffenheimer et al. .......... 422/67 |
| 2003/0152493 A1 * | 8/2003 | Lefebvre .................... 436/180 X |
| 2007/0000337 A1 * | 1/2007 | Gross ........................ 73/864.34 |
| 2008/0275398 A1 * | 11/2008 | Hiebert ........................ 604/131 |
| 2012/0103074 A1 * | 5/2012 | Likuski et al. ........... 73/64.56 X |

FOREIGN PATENT DOCUMENTS

| | | | |
|---|---|---|---|
| JP | 06193555 A * | 7/1994 | ............... 417/122 |
| WO | WO 9631782 A1 * | 10/1996 | |
| WO | WO 9944068 A1 * | 9/1999 | |
| WO | WO 9951980 A2 * | 10/1999 | |
| WO | WO 2004093652 A2 * | 11/2004 | |
| WO | WO 2007106376 A2 * | 9/2007 | |
| WO | WO 2009041826 A1 * | 4/2009 | |

* cited by examiner

*Primary Examiner* — Thomas P Noland
(74) *Attorney, Agent, or Firm* — Advent IP, P.C., L.L.O.

(57) ABSTRACT

A continuous flow syringe pump includes a first syringe configured for at least one of loading or dispensing at least one fluid, a second syringe configured for at least one of loading or dispensing the at least one fluid, and a first valve connected to the first syringe and the second syringe. The continuous flow syringe pump also includes a second valve connected to the first valve. The continuous flow syringe pump further includes at least one outlet connected to the first valve. The at least one outlet is configured to alternate output of the at least one fluid between the first syringe and the second syringe in a substantially continuous operation.

19 Claims, 8 Drawing Sheets

CONTINUOUS FLOW PUMP

FIELD

The present application generally relates to the field of lab instrumentation for chemical analysis, and more particularly to a continuous flow pump.

BACKGROUND

Pumps are utilized to introduce samples carried by carrier solution into nebulizers for further analysis of nebulized liquids in an analytical device such as an inductively coupled plasma mass spectrometry (ICP-MS) spectrometer. When a pump operates with substantial discontinuity of flow, analysis by analytical equipment may be inaccurate and/or unreliable.

SUMMARY

A continuous flow syringe pump includes a first syringe configured for at least one of loading or dispensing at least one fluid, a second syringe configured for at least one of loading or dispensing the at least one fluid, and a first valve connected to the first syringe and the second syringe. The first valve includes at least four ports into or out of which fluid may pass, and is configured for providing fluid to or receiving fluid from each of the first syringe and the second syringe. The continuous flow syringe pump also includes a second valve connected to the first valve. The second valve includes at least four ports into or out of which fluid may pass. The continuous flow syringe pump further includes at least one outlet connected to the first valve. The at least one outlet is configured to alternate output of the at least one fluid between the first syringe and the second syringe in a substantially continuous operation.

A continuous flow pump includes a first syringe device configured for at least one of loading or dispensing at least two fluids. The first syringe device includes a first syringe and a second syringe. The continuous flow pump also includes a second syringe device configured for at least one of loading or dispensing the at least two fluids. The second syringe device includes a third syringe and a fourth syringe. The continuous flow pump additionally includes a first valve connected to the first syringe device and the second syringe device. The first valve includes at least eight ports into or out of which fluid may pass, and is configured for providing fluid to or receiving fluid from each of the first syringe, the second syringe, the third syringe, and the fourth syringe. The continuous flow pump further includes a second valve connected to the first valve. The second valve includes at least four ports into or out of which fluid may pass. The continuous flow pump still further includes at least two outlets connected to the first valve. Each of the at least two outlet configured to alternate output of the at least two fluids between the first syringe device and the second syringe device in a substantially continuous operation.

A sample analysis system includes a continuous flow pump, a sample pump, and an analytical device. The continuous flow pump includes a first syringe configured for at least one of loading or dispensing at least one fluid, a second syringe configured for at least one of loading or dispensing the at least one fluid, and a first valve connected to the first syringe and the second syringe. The first valve includes at least four ports into or out of which fluid may pass, and is configured for providing fluid to or receiving fluid from each of the first syringe and the second syringe. The continuous flow syringe pump also includes a second valve connected to the first valve. The second valve includes at least four ports into or out of which fluid may pass. The continuous flow syringe pump further includes at least one outlet connected to the first valve. The at least one outlet is configured to alternate output of the at least one fluid between the first syringe and the second syringe in a substantially continuous operation. The sample pump is configured to introduce a sample solution to the sample analysis system. The analytical device is configured to analyze the composition of at least the sample solution.

It is to be understood that both the foregoing general description and the following detailed description are exemplary and explanatory only and are not necessarily restrictive as claimed. The accompanying drawings, which are incorporated in and constitute a part of the specification, illustrate an embodiment and together with the general description, serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Figure 1:
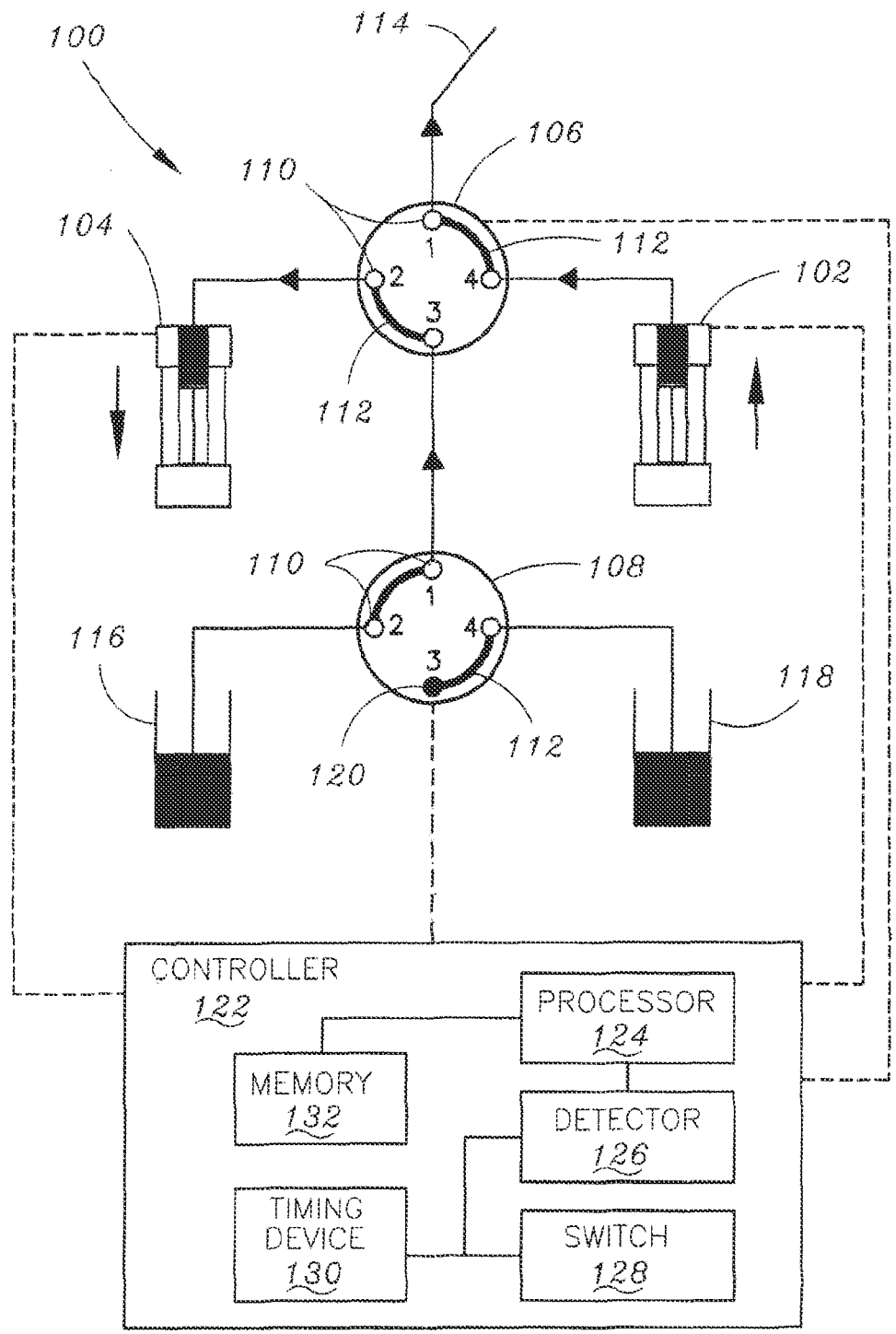
FIG. 1 is a schematic illustration of a first embodiment of a continuous flow pump.

Reference will now be made in detail to the presently preferred embodiments of the disclosure, examples of which are illustrated in the accompanying drawings.

Referring now to FIGS. 1-8, schematic illustrations of a first embodiment of a continuous flow pump 100 are shown. The continuous flow pump 100 may comprise a first syringe 102, a second syringe 104, a first valve 106, and a second valve 108. The first syringe 102 and the second syringe 104 may each be configured for at least one of loading or dispensing at least one fluid. For instance, each syringe may include a barrel and a plunger, where the plunger is configured to create a pressure difference, which may either push fluid out of the barrel by pushing the plunger against the fluid or draw fluid into the barrel by drawing the plunger away from the fluid. In FIGS. 1-8, an arrow next to either of the first syringe 102 or the second syringe 104 indicates that the syringe is loading fluid or dispensing fluid, with a down-facing arrow indicating the loading of fluid into the syringe, whereas an up-facing arrow indicating the dispensing of fluid from the syringe.

It is contemplated that the fluid pumped from the continuous flow pump 100 may be a carrier solution, an internal standard solution, and/or another fluid for use in the analysis of samples in analytical equipment. For instance, a constant flow of fluid may assist in providing a more accurate analysis from analytical equipment. Additionally, a constant flow may enable use of a lower flow rate, while retaining accurate results.

The first valve 106 may be connected to each of the first syringe 102, the second syringe 104, and the second valve 108. The first valve 106 and the second valve 108 may each include a plurality of ports 110. In one embodiment, the first valve 106 and the second valve 108 each include four ports 110 (labeled 1, 2, 3, and 4 in FIGS. 1-8). Each port 110 may be a bi-directional inlet/outlet for fluid passage. The first valve 106 and the second valve 108 may each further include two tube segments 112. The tube segments 112 may be configured to connect two adjacent ports, such that fluid may enter one port, pass through the tube segment, and exit an adjacent port. For example, in FIG. 1, one tube segment 112 of the first valve 106 connects port 1 to port 4, and another tube segment 112 connects port 2 to port 3.

FIG. 1-8 may represent a sequence of operations of the continuous flow pump 100. For instance, the sequence of operations may indicate one cycle of the continuous flow pump 100, which may be repeated to provide continuous flow of a fluid from the continuous flow pump 100. The first valve 106 may operate between at least two operational states for each of the first syringe 102 and the second syringe 104. The at least two operational states may include a loading state and a dispensing state. An additional state may include a ready state, where no substantial operation is occurring during the state, such as when a syringe is fully loaded and awaiting a dispense operation. The tube segments 112 may operate in concert, such that when one tube segment 112 moves to connect two ports 110, then the other tube segment 112 moves to connect two different ports. For example, when one tube segment 112 currently connects ports 1 and 4, then the other tube segment may connect ports 2 and 3. When the first tube segment 112 moves to connect ports 1 and 2, the second tube segment 112 may simultaneously move to connect ports 3 and 4. Such a change may be seen occurring between FIGS. 3 and 4.

An exemplary sequence of operations for each of the first syringe 102, the second syringe 104, the first valve 106, and the second valve 108 will now be explained according to the following description of FIGS. 1-8. In FIG. 1, the first syringe 102 is performing a dispense operation. For instance, the first syringe 102 may pump fluid contained in the barrel of the first syringe 102, through the first valve 106 (e.g., via port 4 through tube segment 112 and out port 1) and out an outlet 114. Here, the first syringe 102 may have approximately 50%-70% of the fluid in the barrel to be dispensed. The second syringe 104 is performing a load operation. For instance, the second syringe 104 may draw fluid into the barrel of the second syringe 104 from a fluid source 116. The fluid source 116 may be a container configured for containing and supplying a fluid to the continuous flow pump 100. In the embodiment shown in FIG. 1, the second syringe 104 draws in fluid from the fluid source 116 via the second valve 108 (via port 2 through tube segment 112 and out port 1) and via the first valve 106 (via port 3 through tube segment 112 and out port 2). The first valve 106 is positioned to allow the first syringe 102 access to the outlet 114 and to allow the second syringe 104 access to the second valve 108. For example, the first valve 106 is in a load position (from the standpoint of the second syringe 104). The second valve 108 is positioned to allow the second syringe 104 access to the fluid source 116 (via the first valve 106). For example, the second valve 108 is in a load position (from the standpoint of the second syringe 104).

Figure 2:
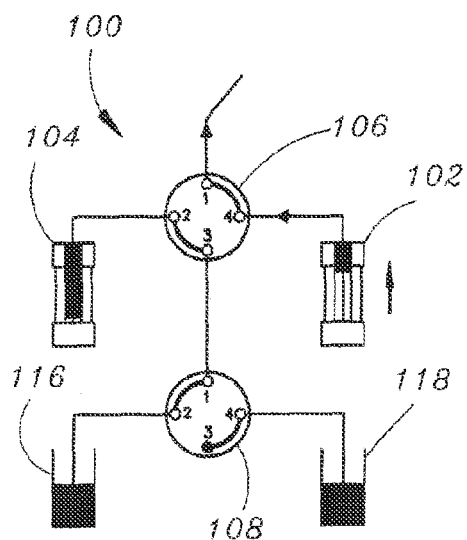
FIG. 2 is a schematic illustration of the continuous flow pump of FIG. 1.

In FIG. 2, the first syringe 102 continues to perform the dispense operation. The first syringe 102 may have approximately 30%-50% of the fluid in the barrel to be dispensed. The second syringe 104 is in a ready state. The ready state may indicate that the second syringe 104 has approximately fully loaded the barrel of the second syringe 104 with fluid and is on standby to dispense the fluid. The second syringe 104 may not dispense the fluid while in the ready state, since the first syringe 102 still has adequate fluid remaining in the barrel to dispense at this point. The first valve 106 is positioned to allow the first syringe 102 access to the outlet 114 and to allow the second syringe 104 access to the second valve 108. For example, the first valve 106 is in a load position (from the standpoint of the second syringe 104). The second valve 108 is positioned to allow the second syringe 104 access to the fluid source 116 (via the first valve 106). For example, the second valve 108 is in a load position (from the standpoint of the second syringe 104). However, since the second syringe 104 is approximately full, fluid may not be flowing from the fluid source 116 to the second syringe 104.

Figure 3:
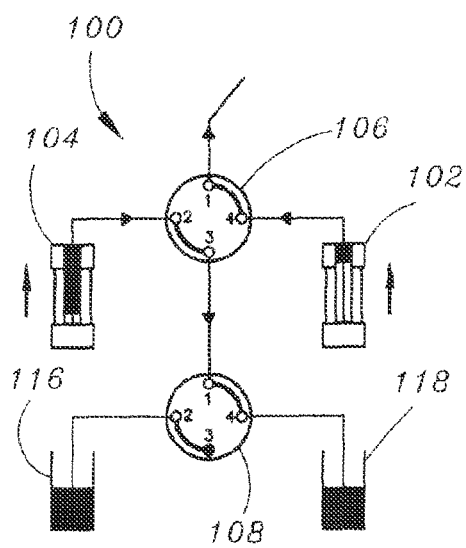
FIG. 3 is a schematic illustration of the continuous flow pump of FIG. 1.

In FIG. 3, the first syringe 102 continues to perform the dispense operation. The first syringe 102 may have approximately 10%-30% of the fluid in the barrel to be dispensed. The second syringe 104 is performing a pre-dispense operation. The pre-dispense operation may indicate that the second syringe 104 is dispensing a portion of fluid to a fluid receptacle 118. The pre-dispense operation may prime the second syringe 104 for eventual dispensing of fluid out of the outlet 114, such as by dispensing a portion of fluid into the fluid receptacle 118 to remove any potential gas pockets from the fluid in the barrel. The second syringe 104 may have approximately 90%-100% of the fluid in the barrel to be dispensed. In the embodiment shown in FIG. 3, the second syringe 104 dispenses fluid through the first valve 106 (via port 2 through tube segment 112 and out port 3) and through the second valve 108 (via port 1 through tube segment 112 and out port 4) to the fluid receptacle 118. The first valve 106 is positioned to allow the first syringe 102 access to the outlet 114 and to allow the second syringe 104 access to the second valve 108. For example, the first valve 106 may still be considered to be in a load position (from the standpoint of the second syringe 104), as no fluid is being dispensed from the second syringe 104 out of the outlet 114 at this point. The second valve 108 is positioned to allow the second syringe 104 access to the fluid receptacle 118 (via the first valve 106).

Figure 4:
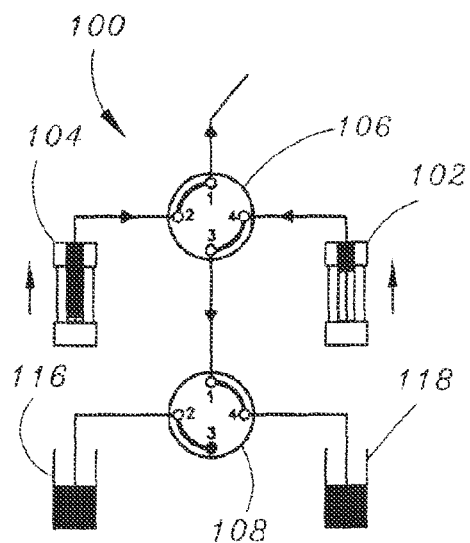
FIG. 4 is a schematic illustration of the continuous flow pump of FIG. 1.

In FIG. 4, the first syringe 102 is performing a post-dispense operation. The post-dispense operation may indicate that the first syringe 102 is dispensing a portion of fluid to the fluid receptacle 118. The first syringe 102 may have approximately 0%-10% of the fluid in the barrel to be dispensed. By performing a post-dispense operation rather than dispensing the entire amount of fluid in the barrel out of the outlet 114, the first syringe 102 may avoid injecting air into the outlet 114. For instance, if the second syringe 104 does not begin dispensing until after the first syringe 102 is approximately empty, then air may be allowed out of the outlet 114 before the second syringe 104 begins dispensing. The second syringe 104 is performing a dispense operation. The second syringe 104 may have approximately 70%-90% of the fluid in the barrel to be dispensed. The first valve 106 is positioned to allow the first syringe 102 access to the second valve 108 and to allow the second syringe 104 access to the outlet 114. The second valve 108 is positioned to allow the first syringe 102 access to the fluid receptacle 118 (via the first valve 106).

Figure 5:
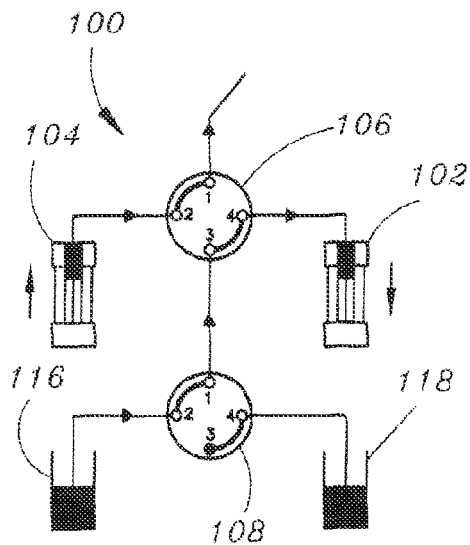
FIG. 5 is a schematic illustration of the continuous flow pump of FIG. 1.

In FIG. 5, the first syringe 102 begins performing a load operation. For instance, the first syringe 102 may draw fluid into the barrel of the first syringe 102 from the fluid source 116. In the embodiment shown in FIG. 5, the first syringe 102 draws in fluid from the fluid source 116 via the second valve 108 (via port 2 through tube segment 112 and out port 1) and via the first valve 106 (via port 3 through tube segment 112 and out port 4). The second syringe 104 continues to perform the dispense operation. The second syringe 104 may have approximately 50%-70% of the fluid in the barrel to be dispensed. The first valve 106 is positioned to allow the first syringe 102 access to the second valve 108 and to allow the second syringe 104 access to the outlet 114. The second valve 108 is positioned to allow the first syringe 102 access to the fluid source 116 (via the first valve 106).

Figure 6:
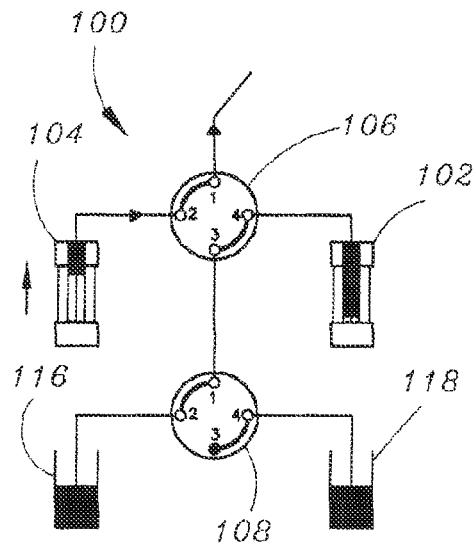
FIG. 6 is a schematic illustration of the continuous flow pump of FIG. 1.

In FIG. 6, the first syringe 102 is in a ready state. The ready state may indicate that the first syringe 102 has approximately fully loaded the barrel of the first syringe 102 with fluid and is on standby to dispense the fluid. The first syringe 102 not dispense the fluid while in the ready state, since the second syringe 104 still has adequate fluid remaining in the barrel to dispense at this point. The second syringe 104 continues to perform the dispense operation. The second syringe 104 may have approximately 30%-50% of the fluid in the barrel to be dispensed. The first valve 106 is positioned to allow the first syringe 102 access to the second valve 108 and to allow the second syringe 104 access to the outlet 114. The second valve 108 is positioned to allow the first syringe 102 access to the fluid source 116 (via the first valve 106). However, since the first syringe 102 is approximately full, fluid may not be flowing from the fluid source 116 to the first syringe 102.

Figure 7:
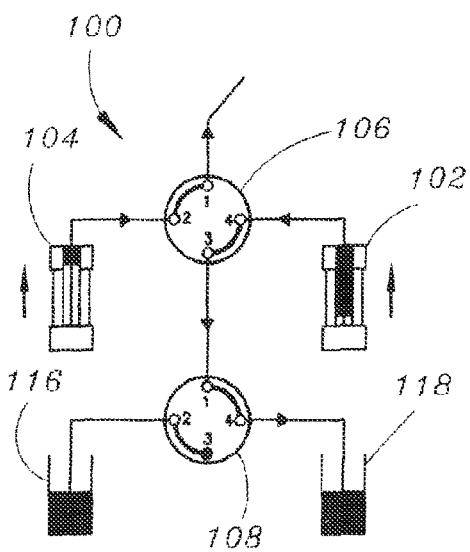
FIG. 7 is a schematic illustration of the continuous flow pump of FIG. 1.

In FIG. 7, the first syringe 102 is performing a pre-dispense operation. The pre-dispense operation may indicate that the first syringe 102 is dispensing a portion of fluid to the fluid receptacle 118. The pre-dispense operation may prime the first syringe 102 for eventual dispensing of fluid out of the outlet 114, such as by dispensing a portion of fluid into the fluid receptacle 118 to remove any potential gas pockets from the fluid in the barrel. The first syringe 102 may have approximately 90%-100% of the fluid in the barrel to be dispensed. In the embodiment shown in FIG. 3, the first syringe 102 dispenses fluid through the first valve 106 (via port 4 through tube segment 112 and out port 3) and through the second valve 108 (via port 1 through tube segment 112 and out port 4) to the fluid receptacle 118. The second syringe 104 continues to perform the dispense operation. The second syringe 104 may have approximately 10%-30% of the fluid in the barrel to be dispensed. The first valve 106 is positioned to allow the first syringe 102 access to the second valve 108 and to allow the second syringe 104 access to the outlet 114. The second valve 108 is positioned to allow the first syringe 102 access to the fluid receptacle 118 (via the first valve 106).

Figure 8:
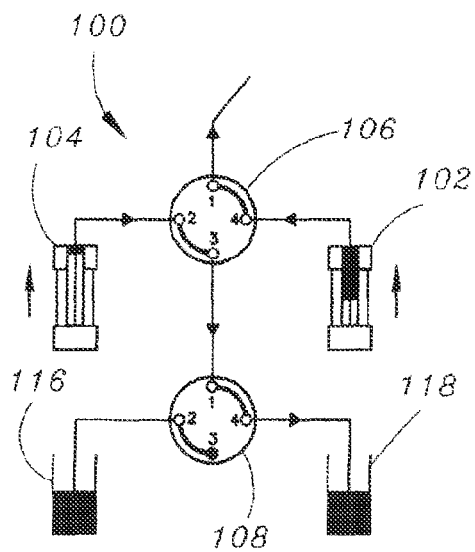
FIG. 8 is a schematic illustration of the continuous flow pump of FIG. 1.

In FIG. 8, the first syringe 102 is performing a dispense operation. For instance, the first syringe 102 may have just switched from the pre-dispense operation, such as that shown in FIG. 7. The first syringe 102 may have approximately 70%-90% of the fluid in the barrel to be dispensed. The second syringe 104 is performing a post-dispense operation. The post-dispense operation may indicate that the second syringe 104 is dispensing a portion of fluid to the fluid receptacle 118. The second syringe 104 may have approximately 0%-10% of the fluid in the barrel to be dispensed. By performing a post-dispense operation rather than dispensing the entire amount of fluid in the barrel out of the outlet 114, the second syringe 104 may avoid injecting air into the outlet 114. For instance, if the first syringe 102 does not begin dispensing until after the second syringe 104 is approximately empty, then air may be allowed out of the outlet 114 before the first syringe 102 begins dispensing. The first valve 106 is positioned to allow the first syringe 102 access to the outlet 114 and to allow the second syringe 104 access to the second valve 108. The second valve 108 is positioned to allow the second syringe 104 access to the fluid receptacle 118 (via the first valve 106).

The sequence of operations represented by FIGS. 1-8 may then be repeated to allow the continuous flow pump 100 to continuously dispense fluid through outlet 114. For example, the operations of the first syringe 102, the second syringe 104, the first valve 106, and the second valve 108 may transition from the positions in FIG. 8 to those of FIG. 1 to continue/restart the sequence of operations. By cycling between dispensing and filling each of the first syringe 102 and the second syringe 104 in an approximately alternate manner, such as in a manner represented by FIGS. 1-8, the continuous flow pump 100 may continuously output fluid without substantial addition of gas.

The continuous flow pump 100 may additionally include a port-blocking device 120 of the second valve 108. The port-blocking device 120 may be configured to prevent fluid flow through a port 110 of the second valve 108, such as when access to a portion of the continuous flow pump 100 is desirably blocked. For example, the port-blocking device 120 may be utilized to prevent access to the fluid receptacle 118 when one syringe is in a ready state and the other syringe is in a dispensing state (such as in FIG. 2), or the port-blocking device 120 may be utilized to prevent access to the fluid source 116 when one syringe is in a pre-dispense state and the other syringe is in a dispense state (such as in FIG. 3), or the port blocking device 120 may be utilized to prevent access to the fluid receptacle 118 when one syringe is in a loading state and the other syringe is in a dispensing state (such as in FIG. 5).

It is contemplated that a controller 122 may be utilized to control the functionality of at least one of the first syringe 102, the second syringe 104, the first valve 106, and the second valve 108. For instance, the controller 122 may execute instructions (e.g., computer language programming) directed to controlling the continuous flow pump 100, such as by performing the sequence of operations, as described in FIGS. 1-8. The controller 122 may include a processor 124, a detector 126, a switch 128, a timing device 130, and a memory 132 as shown in FIG. 1. The processor 124 may be configured to execute the instructions, which may be stored in memory 132.

The detector 126 may be configured to detect a volume of fluid in at least one of the first syringe 102 or the second syringe 104. Alternatively, the detector 126 may be configured to detect a rate of flow dispensing from at least one of the first syringe 102, the second syringe 104, or the outlet 114. For example, the detector 126 may be at least one of a sensor, a flow meter, or another device suitable to detect properties of a fluid, including a volume, a weight, a flow rate, and the like.

The switch 128 may be configured to change the operation of the first syringe 102, the second syringe 104, the first valve 106, and/or the second valve 108. For example, regarding the first syringe 102 and the second syringe 104, the switch 128 may toggle the syringe from a dispensing state to a loading state, from a loading state to a ready state, and from a ready state to a dispensing state. In one embodiment, the switch 128 may control the direction and rate of travel of the plunger within the barrel of the first syringe 102 and/or the second syringe 104 in order to toggle the syringe between operating states. Additionally, regarding the first valve 106, and the second valve 108, the switch 128 may toggle the valve between a loading state and a dispensing state. For instance, the switch 128 may reposition the tube segments 112 within the valve to change which ports are connected depending on the operating state to be performed by the respective valve.

The controller 122 may also include a timing device 130, which may enable the controller 122 to activate the switch 128 based on an elapsed amount of time, or at a specified time. For example, the detector 126 may detect a flow rate, and based on that flow rate, the timing device 130 or the processor 124 may derive a time when a syringe contains a certain percentage of fluid remaining in the barrel. The derived time may be used to switch operating states of the syringe. Additionally, the timing device 130 may be used in conjunction with the detector 124 and the switch 128 to determine a rate of flow (at the outlet 114 or out of each syringe) over a given time period, or to track at what time or at what time interval a syringe and/or a valve is operated and/or switched. Such data may be stored in the memory 132.

One or more of the first syringe 102, the second syringe 104, the first valve 106, and the second valve 108 may include a mechanical and/or electrical connection to support an interface with the controller 122. Such connection capability may enable the first syringe 102, the second syringe 104, the first valve 106, and the second valve 108 to be controlled by the controller 122, such as by enabling the controller 122 to change operating states. Thus, the sequence of operations of FIGS. 1-8 may occur automatically, such as via a computer-controlled system, wherein each of the first syringe 102, the second syringe 104, the first valve 106, and the second valve 108 are automatically controlled.

FIG. 9-16 may represent a second embodiment of a sequence of operations of a continuous flow pump 200. For instance, the second embodiment of sequence of operations may indicate one cycle of the continuous flow pump 200, which may be repeated to provide continuous flow of one or more fluids from the continuous flow pump 200. In the second embodiment, the continuous flow pump 200 may include a first syringe device 202 (e.g., a first syringe pump), a second syringe device 204 (e.g., a second syringe pump), a first valve 206, and a second valve 208. In the second embodiment, the continuous flow pump 200 may manage two fluids, an internal standard solution and a carrier solution. Each of the two fluids may be distributed in the continuous flow pump 200 via separate lines, tubing, etc. Such separation may provide a contamination-free environment, such as to avoid erroneous results via an analysis of a sample in a sample analysis system. Transfer of fluid within the continuous flow pump 200 during each stage of the sequence of operations may be indicated by arrows, which may indicate a direction of fluid travel.

The first syringe device 202 may include a first syringe 202a and a second syringe 202b, each of which may include a barrel and a plunger for drawing fluid in and dispensing fluid out of the barrel. The second syringe device 204 also may include a first syringe 204a and a second syringe 204b. In the second embodiment, lines 207a and syringes 202a and 204a are dedicated to the transport and pumping of a first fluid over the sequence of operations which may indicate one cycle of the continuous flow pump 200. In this embodiment, the first fluid may be a carrier solution. Lines 207b and syringes 202b and 204b are dedicated to the transport and pumping of a second fluid over the sequence of operations which may indicate one cycle of the continuous flow pump 200. In this embodiment, the second fluid may be an internal standard solution.

In the embodiments shown in FIGS. 9-16, the first syringe 202a and the second syringe 202b are configured to load fluid simultaneously and to dispense fluid simultaneously. This simultaneous loading and dispensing may be configured to produce a substantially similar flow rate for each of the first fluid and the second fluid. However, it is contemplated that the flow rates may be differentiated, such as by utilizing differing plunger and barrel sizes for the first syringe 202a and the second syringe 202b. Similarly, the first syringe 204a and the second syringe 204b may be configured to load fluid simultaneously and to dispense fluid simultaneously.

The first valve 206 may be connected to each of the first syringe device 202, the second syringe device 204, and the second valve 208. The first valve 206 and the second valve 208 may each include a plurality of ports 210. In one embodiment, the first valve 206 includes at least eight ports 210 and the second valve 208 includes at least four ports 210. In the embodiments shown in FIGS. 9-16, each of the first valve 206 and the second valve 208 include ten ports 210. Each port 210 may be a bi-directional inlet/outlet for fluid passage. For instance, the ten ports 210 may be utilized to separate portions of the continuous flow pump 200 in order to dedicate one portion of the continuous flow pump 200 to the first fluid and to dedicate another portion to the second fluid. The first valve 206 and the second valve 208 may each further include tube segments 212. The tube segments 212 may be configured to connect two adjacent ports, such that fluid may enter one port, pass through the tube segment, and exit an adjacent port. Such a configuration may be similar to that described in reference to FIGS. 1-8, however, more tube segments 212 may be required, as more ports may be configured to be simultaneously utilized in continuous flow pump 200 than in continuous flow pump 100.

The first valve 206 may operate between two operating positions, a load position (as seen in FIGS. 9, 10, 11, and 16) and a dispense position (as seen in FIGS. 12, 13, 14, and 15). The two operating positions may depend on the positioning of the tube segments 212 within the first valve 206. The second valve 208 may also operate between two operating positions, a load position (as seen in FIGS. 9, 10, 12, and 15) and a dispense position (as seen in FIGS. 11, 13, 14, and 16). The load and dispense labeling of the two operating positions may be taken from a perspective of the second syringe device 204. For instance, when the first valve 206 is in a load position, the second syringe device 204 may be loading the first syringe 204a and the second syringe 204b, or may have recently finished loading and is performing a pre-dispense operation.

Figure 9:
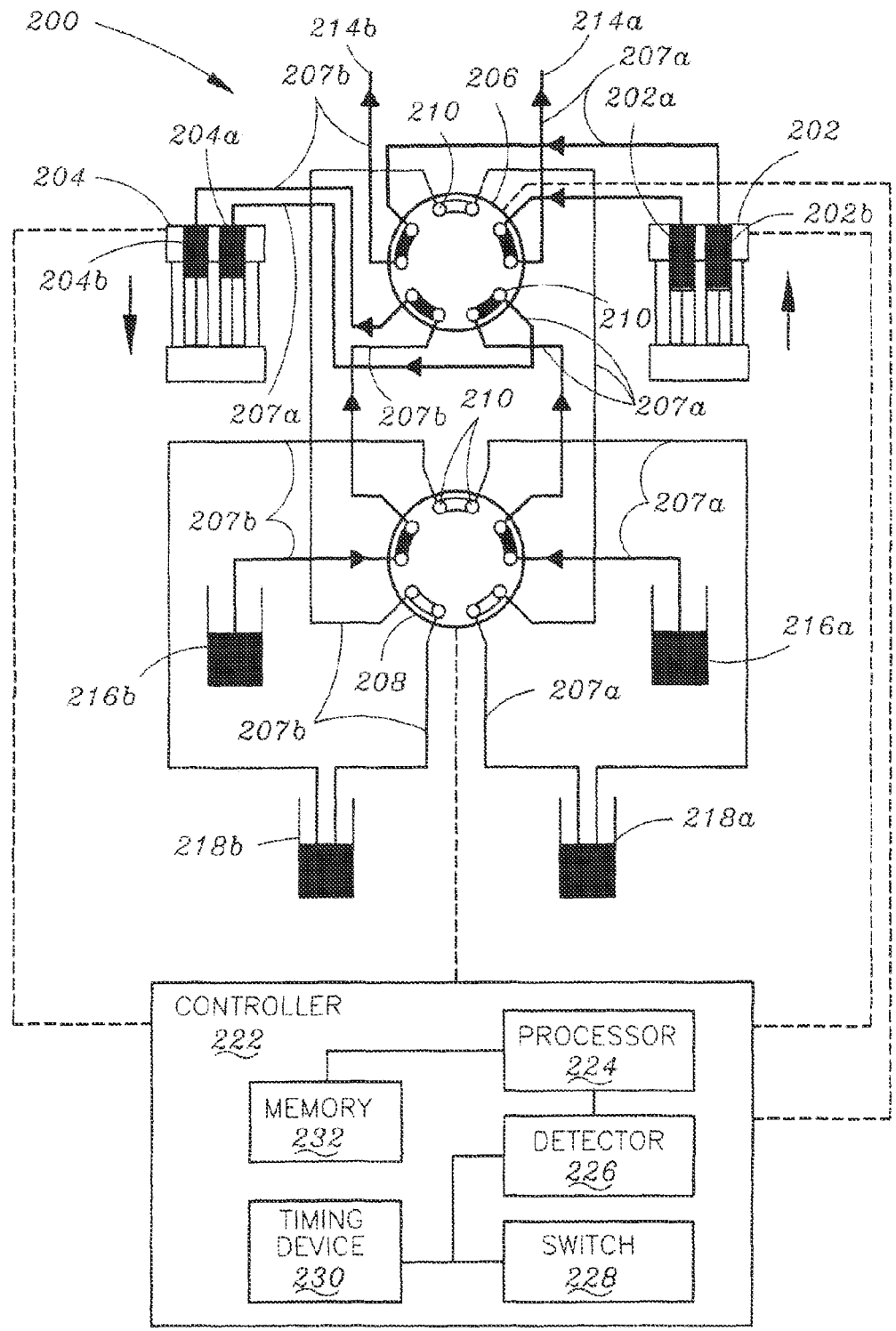
FIG. 9 is a schematic illustration of a second embodiment of a continuous flow pump.

An exemplary sequence of operations for each of the first syringe device 202, the second syringe device 204, the first valve 206, and the second valve 208 will now be explained according to the following description of FIGS. 9-16. In FIG. 9, the first syringe device 202 is performing a dispense operation. For instance, the first syringe device 202 may pump fluid contained in the barrels of the first syringe 202a and the second syringe 202b, through the first valve 206 and out one of outlet 214a or 214b. Outlet 214a may provide an outlet for the carrier solution which was located in syringe 202a or 204a. Outlet 214b may provide an outlet for the internal standard solution which was located in syringe 202b or 204b. The first syringe 202a and the second syringe 202b may have approximately 50%-70% of the fluid in the barrel to be dispensed. The second syringe device 204 is performing a load operation. For instance, the second syringe device 204 may draw fluid into the barrel of the first syringe 204a and the second syringe 204b from a fluid source 216a and a fluid source 216b, respectively. The fluid sources 216a and 216b may be containers configured for containing and supplying a fluid to the continuous flow pump 200. For instance, the fluid source 216a may be a fluid source for carrier solution, whereas the fluid source 216b may be a fluid source for internal standard solution. In the embodiment shown in FIG. 9, the second syringe device 204 draws in fluid from fluid source 216a and fluid source 216b via the second valve 208 and via the first valve 206. The first valve 206 is positioned to allow the first syringe device 202 access to outlet 214a and outlet 214b and to allow the second syringe device 204 access to the second valve 208. For example, the first valve 206 is in a load position (from the standpoint of the second syringe device 204). The second valve 208 is positioned to allow the second syringe device 204 access to fluid source 216a and fluid source 216b (via the first valve 206). For example, the second valve 208 is in a load position (from the standpoint of the second syringe device 204).

Figure 10:
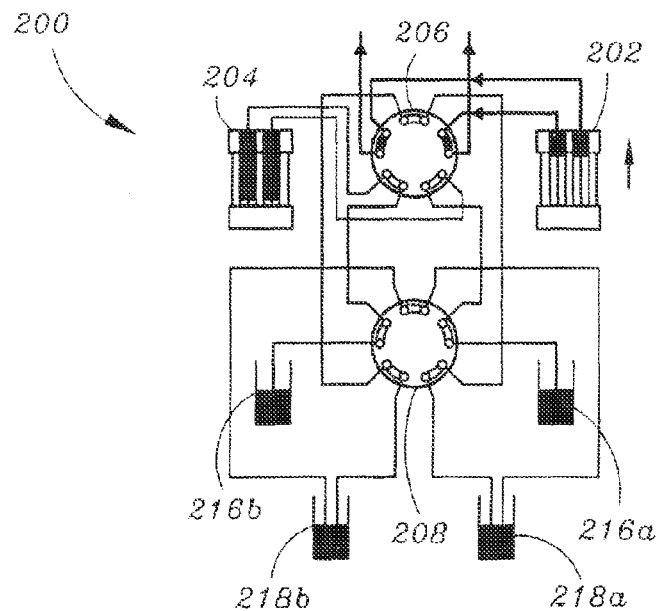
FIG. 10 is a schematic illustration of the continuous flow pump of FIG. 9.

In FIG. 10, the first syringe device 202 continues to perform the dispense operation. The first syringe 202a and the second syringe 202b may each have approximately 30%-50% of the fluid in the barrel to be dispensed. The second syringe device 204 is in a ready state. The ready state may indicate that the second syringe device 204 has approximately fully loaded the barrels of the first syringe 204a and the second syringe 204b with fluid(s) and is on standby to dispense the fluid(s). The second syringe device 204 may not dispense the fluid while in the ready state, since the syringes (202a and 202b) of the first syringe device 202 still contain adequate fluid in the barrels to dispense at this point. The first valve 206 is positioned to allow the first syringe device 202 access to outlet 214a and outlet 214b and to allow the second syringe device 204 access to the second valve 208. For example, the first valve 206 is in a load position (from the standpoint of the second syringe device 204). The second valve 208 is positioned to allow the second syringe device 204 access to fluid source 216a and fluid source 216b (via the first valve 206). For example, the second valve 208 is in a load position (from the standpoint of the second syringe device 204). However, since the second syringe device 204 is approximately full, fluid may not be flowing from fluid source 216a and fluid source 216b to the second syringe device 204.

Figure 11:
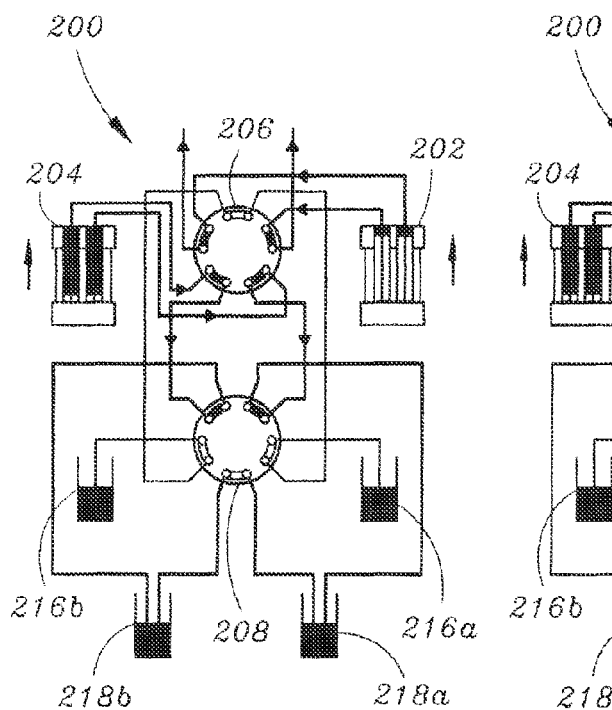
FIG. 11 is a schematic illustration of the continuous flow pump of FIG. 9.

In FIG. 11, the first syringe device 202 continues to perform the dispense operation. The first syringe 202a and the second syringe 202b may each have approximately 10%-30% of the fluid in the barrel to be dispensed. The second syringe device 204 is performing a pre-dispense operation. The pre-dispense operation may indicate that the second syringe device 204 is dispensing a portion of fluid to a fluid receptacle 218a and to a fluid receptacle 218b, where fluid from the first syringe 204a is directed to fluid receptacle 218a and fluid from the second syringe 204b is directed to fluid receptacle 218b. The pre-dispense operation may prime the second syringe device 204 for eventual dispensing of fluid out of outlet 214a and 214b, such as by dispensing a portion of fluid into fluid receptacle 218a and fluid receptacle 218b to remove any potential gas pockets from the fluid in the barrel of syringes 204a and 204b. The first syringe 204a and the second syringe 204b may each have approximately 90%-100% of the fluid in the barrel to be dispensed. In the embodiment shown in FIG. 11, the second syringe device 204 dispenses fluid through the first valve 206 and through the second valve 208 to the fluid receptacles 218a and 218b. The first valve 206 is positioned to allow the first syringe device 202 access to outlets 214a and 214b and to allow the second syringe device 204 access to the second valve 208. For example, the first valve 206 may still be considered to be in a load position (from the standpoint of the second syringe device 204), as no fluid is being dispensed from the second syringe device 204 out of outlet 214a or 214b at this point. The second valve 208 is positioned to allow the second syringe device 204 access to fluid receptacles 218a and 218b (via the first valve 206).

Figure 12:
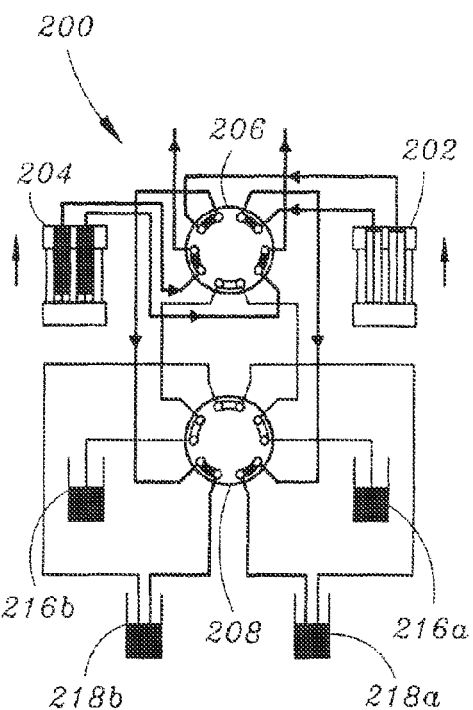
FIG. 12 is a schematic illustration of the continuous flow pump of FIG. 9.

In FIG. 12, the first syringe device 202 is performing a post-dispense operation. The post-dispense operation may indicate that the first syringe 202a and the second syringe 202b are dispensing a portion of fluid to fluid receptacle 218a and 218b, respectively. The first syringe 202a and the second syringe 202b may each have approximately 0%-10% of the fluid in the barrel to be dispensed. By performing a post-dispense operation rather than dispensing the entire amount of fluid in the barrels out of outlet 214a and 214b, the first syringe device 202 may avoid injecting air into outlet 214a and/or 214b. For instance, if the second syringe device 204 does not begin dispensing until after the first syringe device 202 is approximately empty, then air may be allowed out of outlet 214a and/or 214b before the second syringe device 204 begins dispensing. The second syringe device 204 is performing a dispense operation. The first syringe 204a and the second syringe 204b may each have approximately 70%-90% of the fluid in the barrel to be dispensed. The first valve 206 is positioned to allow the first syringe device 202 access to the second valve 208 and to allow the second syringe 204 access to outlet 214a and 214b. The second valve 208 is positioned to allow the first syringe device 202 access to fluid receptacles 218a and 218b (via the first valve 206).

Figure 13:
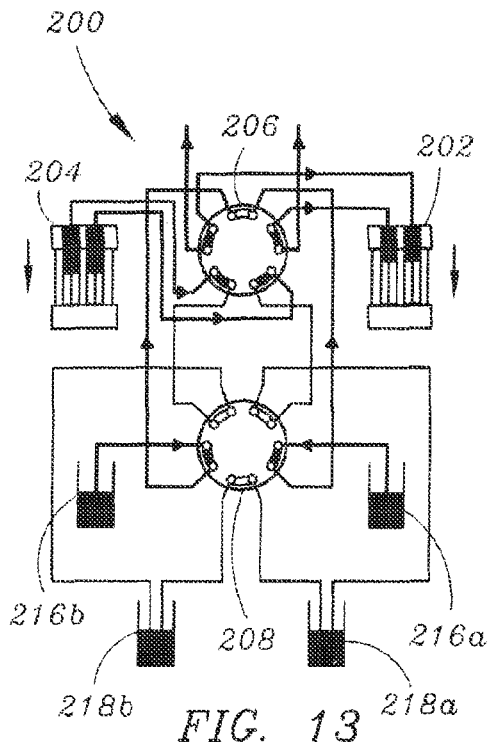
FIG. 13 is a schematic illustration of the continuous flow pump of FIG. 9.

In FIG. 13, the first syringe device 202 begins performing a load operation. For instance, the first syringe device 202 may draw fluid into the barrel of the first syringe 202a and into the barrel of the second syringe 202b from fluid source 216a and 216b, respectively. In the embodiment shown in FIG. 13, the first syringe device 202 draws in fluid from fluid sources 216a and 216b via the second valve 208 and via the first valve 206. The second syringe device 204 continues to perform the dispense operation. The first syringe 204a and the second syringe 204b may each have approximately 50%-70% of the fluid in the barrel to be dispensed. The first valve 206 is positioned to allow the first syringe device 202 access to the second valve 208 and to allow the second syringe device 204 access to outlet 214a and 214b. The second valve 208 is positioned to allow the first syringe device 202 access to fluid source 216a and 216b (via the first valve 206).

Figure 14:
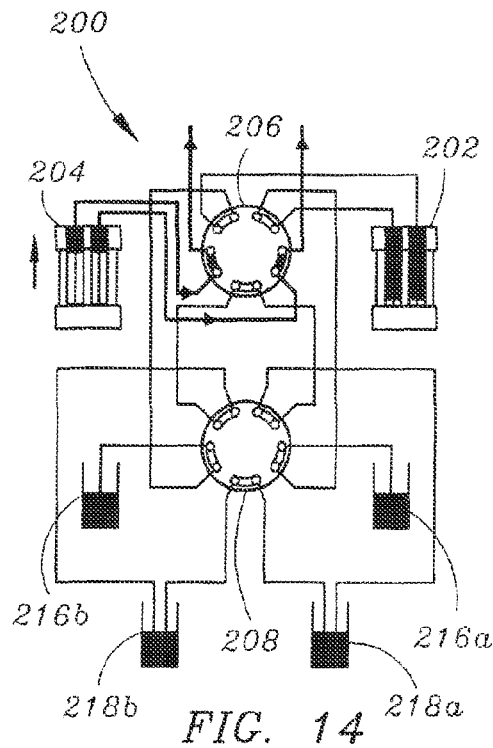
FIG. 14 is a schematic illustration of the continuous flow pump of FIG. 9.

In FIG. 14, the first syringe device 202 is in a ready state. The ready state may indicate that the first syringe device 202 has approximately fully loaded the barrel of the first syringe 202a and of the second syringe 202b with fluid and is on standby to dispense the fluid. The first syringe device 202 not dispense the fluid while in the ready state, since the second syringe device 204 still has adequate fluid remaining in the barrels to dispense at this point. The second syringe device 204 continues to perform the dispense operation. The first syringe 204*a* and the second syringe device 204*b* may each have approximately 30%-50% of the fluid in the barrel to be dispensed. The first valve 206 is positioned to allow the first syringe device 202 access to the second valve 208 and to allow the second syringe device 204 access to outlet 214*a* and 214*b*. The second valve 208 is positioned to allow the first syringe device 202 access to fluid source 216*a* and to fluid source 216*b* (via the first valve 206). However, since the first syringe 202*a* and the second syringe 202*b* are approximately full, fluid may not be flowing from fluid source 216*a* and 216*b* to the first syringe device 202.

Figure 15:
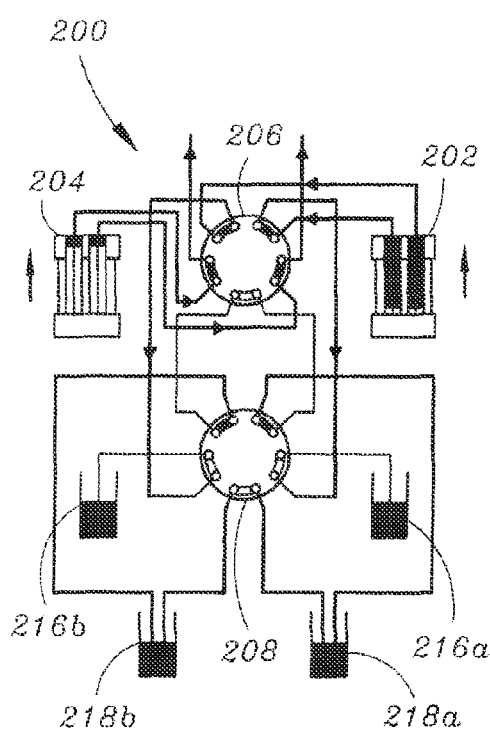
FIG. 15 is a schematic illustration of the continuous flow pump of FIG. 9.

In FIG. 15, the first syringe device 202 is performing a pre-dispense operation. The pre-dispense operation may indicate that the first syringe device 202 is dispensing a portion of fluid from the first syringe 202*a* and from the second syringe 202*b* to fluid receptacle 218*a* and to fluid receptacle 218*b*, respectively. The pre-dispense operation may prime the first syringe device 202 for eventual dispensing of fluid out of outlet 214*a* and 214*b*, such as by dispensing a portion of fluid into fluid receptacle 218*a* and 218*b* to remove any potential gas pockets from the fluid in the barrel of syringes 204*a* and 204*b*. The first syringe 202*a* and the second syringe 202*b* may each have approximately 90%-100% of the fluid in the barrel to be dispensed. In the embodiment shown in FIG. 15, the first syringe device 202 dispenses fluid through the first valve 206 and through the second valve 208 to fluid receptacle 218*a* and fluid receptacle 218*b*. The second syringe device 204 continues to perform the dispense operation. The first syringe 204*a* and the second syringe 204*b* may each have approximately 10%-30% of the fluid in the barrel to be dispensed. The first valve 206 is positioned to allow the first syringe device 202 access to the second valve 208 and to allow the second syringe device 204 access to outlets 214*a* and 214*b*. The second valve 208 is positioned to allow the first syringe device 202 access to fluid receptacle 218*a* and to fluid receptacle 218*b* (via the first valve 206).

Figure 16:
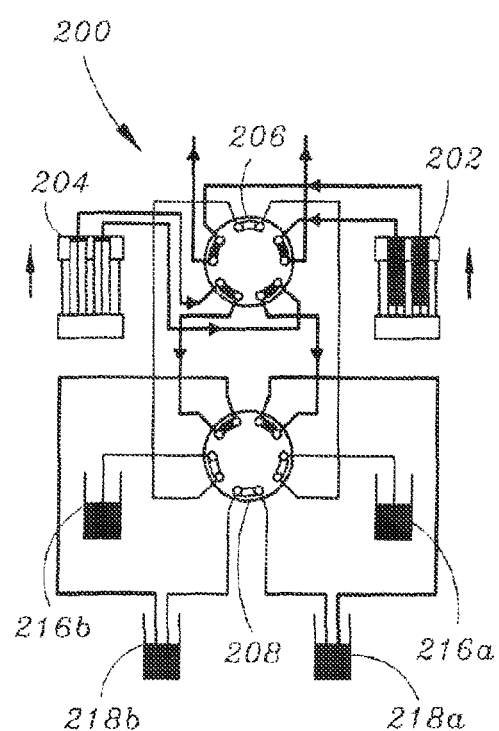
FIG. 16 is a schematic illustration of the continuous flow pump of FIG. 9.

In FIG. 16, the first syringe device 202 is performing a dispense operation. For instance, the first syringe device 102 may have just switched from the pre-dispense operation, such as that shown in FIG. 15. The first syringe 202*a* and the second syringe 202*b* may each have approximately 70%-90% of the fluid in the barrel to be dispensed. The second syringe device 204 is performing a post-dispense operation. The post-dispense operation may indicate that the second syringe device 204 is dispensing a portion of fluid in the first syringe 204*a* and in the second syringe 204*b* to fluid receptacle 218*a* and to fluid receptacle 218*b*, respectively. The first syringe 204*a* and the second syringe 204*b* may each have approximately 0%-10% of the fluid in the barrel to be dispensed. By performing a post-dispense operation rather than dispensing the entire amount of fluid in the barrels of the first syringe 204*a* and the second syringe 204*b* out of outlet 214*a* and 214*b*, respectively, the second syringe device 204 may avoid injecting air into outlet 214*a* and 214*b*. For instance, if the first syringe device 202 does not begin dispensing until after the second syringe device 204 is approximately empty, then air may be allowed out of outlet 214*a* and 214*b* before the first syringe device 202 begins dispensing. The first valve 216 is positioned to allow the first syringe device 202 access to outlet 214*a* and 214*b* and to allow the second syringe device 204 access to the second valve 208. The second valve 208 is positioned to allow the second syringe device 104 access to fluid receptacle 218*a* and to fluid receptacle 218*b* (via the first valve 206).

The sequence of operations represented by FIGS. 9-16 may then be repeated to allow the continuous flow pump 200 to continuously dispense fluid through outlet 214*a* and outlet 214*b*. For example, the operations of the first syringe device 202, the second syringe device 204, the first valve 206, and the second valve 208 may transition from the positions in FIG. 16 to those of FIG. 9 to continue/restart the sequence of operations. By cycling between dispensing and filling each of the first syringe device 202 and the second syringe device 204 in an approximately alternate manner, such as in a manner represented by FIGS. 9-16, the continuous flow pump 200 may continuously output fluid without substantial addition of gas.

It is contemplated that a controller 222 may be utilized to control the functionality of at least one of the first syringe device 202, the second syringe device 204, the first valve 206, or the second valve 208. For instance, the controller 222 may execute instructions (e.g., computer language programming) directed to controlling the continuous flow pump 200, such as by performing the sequence of operations, as described in FIGS. 9-16. The controller 222 may include a processor 224, a detector 226, a switch 228, a timing device 230, and a memory 232 as shown in FIG. 1. The processor 224 may be configured to execute the instructions, which may be stored in memory 232.

The detector 226 may be configured to detect a volume of fluid in at least one of the first syringe 202*a*, the second syringe 202*b*, the first syringe 204*a*, or the second syringe 204*b*. Alternatively, the detector 226 may be configured to detect a rate of flow dispensing from at least one of first syringe 202*a*, the second syringe 202*b*, the first syringe 204*a*, the second syringe 204*b*, outlet 214*a*, or outlet 214*b*. For example, the detector 226 may be at least one of a sensor, a flow meter, or another device suitable to detect properties of a fluid, including a volume, a weight, a flow rate, or the like.

The switch 228 may be configured to change the operation of the first syringe device 202, the second syringe device 204, the first valve 206, and/or the second valve 208. For example, regarding the first syringe device 202 and the second syringe device 204, the switch 228 may toggle the syringe device from a dispensing state to a loading state, from a loading state to a ready state, and from a ready state to a dispensing state. In one embodiment, the switch 228 may control the direction and rate of travel of the plunger within the barrel of the first syringe 202*a*, the second syringe 202*b*, the first syringe 204*a*, and/or the second syringe 204*b* in order to toggle the syringe between operating states. Additionally, regarding the first valve 206, and the second valve 208, the switch 228 may toggle the valve between a loading state and a dispensing state. For instance, the switch 228 may which ports 210 are connected depending on the operating state to be performed by the respective valve.

The controller 222 may also include a timing device 230, which may enable the controller 222 to activate the switch 228 based on an elapsed amount of time, or at a specified time. For example, the detector 226 may detect a flow rate, and based on that flow rate, the timing device 230 or the processor 224 may derive a time when a syringe contains a certain percentage of fluid remaining in the barrel. The derived time may then be used to switch operating states of the syringe. Additionally, the timing device 230 may be used in conjunction with the detector 224 and the switch 228 to determine a rate of flow (at outlet 214*a* or outlet 214*b* or out of each syringe) over a given time period, or to track at what time or at what time interval a syringe and/or a valve is operated and/or switched. Such data may be stored in the memory 232.

One or more of the first syringe device 202, the second syringe device 204, the first valve 206, and the second valve 208 may include a mechanical and/or electrical connection to support an interface with the controller 222. Such connection capability may enable the first syringe device 202, the second syringe device 204, the first valve 206, and the second valve 208 to be controlled by the controller 222, such as by enabling the controller 222 to change operating states. Thus, the sequence of operations of FIGS. 9-16 may occur automatically, such as via a computer-controlled system, wherein each of the first syringe device 202, the second syringe device 204, the first valve 206, and the second valve 208 are automatically controlled.

Figure 17:
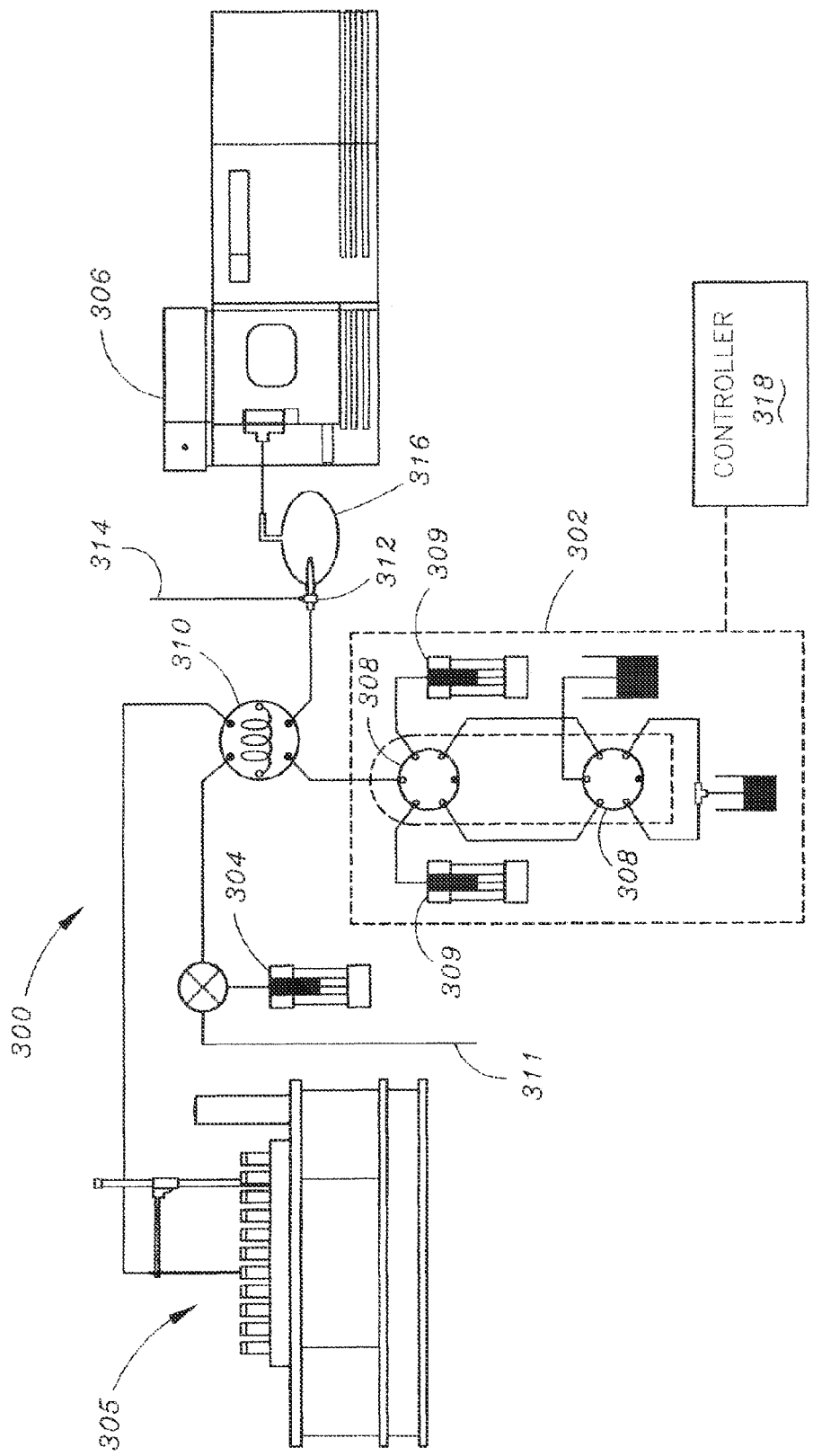
FIG. 17 is a schematic illustration of a sample analysis system, according to an exemplary embodiment of the present disclosure.

Referring now to FIG. 17, a schematic illustration of a sample analysis system 300 is shown according to an exemplary embodiment of the present disclosure. The sample analysis system 300 includes a continuous flow pump 302, a sample pump 304, and an analytical device 306. The continuous flow pump 302 may function similarly to the continuous flow pump 100 and/or the continuous flow pump 200, as described above with reference to FIGS. 1-8 and 9-16, respectively. For instance, at least two syringes may be alternately loaded and dispensed via two valves to continuously output fluid without substantial addition of gas, while maintaining a clean and low flow rate of fluid. While the continuous flow pump 302 is shown in FIG. 17 with two 6-port valves 308 and two syringes 309, it may be appreciated that other suitable valve and syringe configurations may be utilized. The sample pump 304 may be configured to introduce a sample solution to the sample analysis system 300. For example, a sample may be drawn from an auto sampler 305, and introduced into the sample analysis system 300 by the sample pump 304, such as by forming a sample solution from solution contained in the sample pump 304. The analytical device 306 may be configured to analyze the composition of the sample solution. For instance, the analytical device 306 may be an inductively coupled plasma mass spectrometry (ICP-MS) spectrometer, or other device sufficient to analyze the composition of the sample solution.

The sample analysis system 300 may also include a system valve 310. The system valve 308 may be configured to couple between each of the continuous flow pump 302, the sample pump 304, and the analytical device 306. The system valve 308 may be operable to selectively permit fluid flow between the continuous flow pump 302, the sample pump 304, the auto sampler 305, and the analytical device 306. The sample analysis system 300 may include lines with matched restriction. The lines may include those within the continuous flow pump 302 and the line leading from the continuous flow pump 302 to the system valve 308. For instance, a matched restriction may indicate one or more of a matching line diameter, low pressurization, and substantially no pressurization. The sample analysis system 300 may also include a waste line 311.

The sample analysis system 300 may further include a nebulizer 312. The nebulizer 312 may include a gaseous feed source 314 to assist in atomizing the fluid fed into the nebulizer 312. For example, the gaseous feed source 314 may feed argon into the nebulizer at a constant feed rate. However, it may be appreciated that a variety of gases and mixtures of gases may be provided to the nebulizer 312 depending on the fluids to be tested by the analytical device 306. The nebulizer 312 may also be coupled with a spray chamber 316. The spray chamber 316 may further prepare the sample to be tested in the analytical device 306, such as by filtering the sample mist to permit an appropriate droplet size distribution to feed into the analytical device 306. For instance, the spray chamber 316 may be a high-efficiency cyclonic spray chamber.

The sample analysis system 300 may additionally include a controller 318 configured to control the operation of the continuous flow pump 302. The controller 318 may operate substantially similar to the controller 122 of the continuous flow pump 100 and/or to the controller 222 of the continuous flow pump 200, as shown in FIGS. 1 and 9, respectively, and described above.

Figure 18:
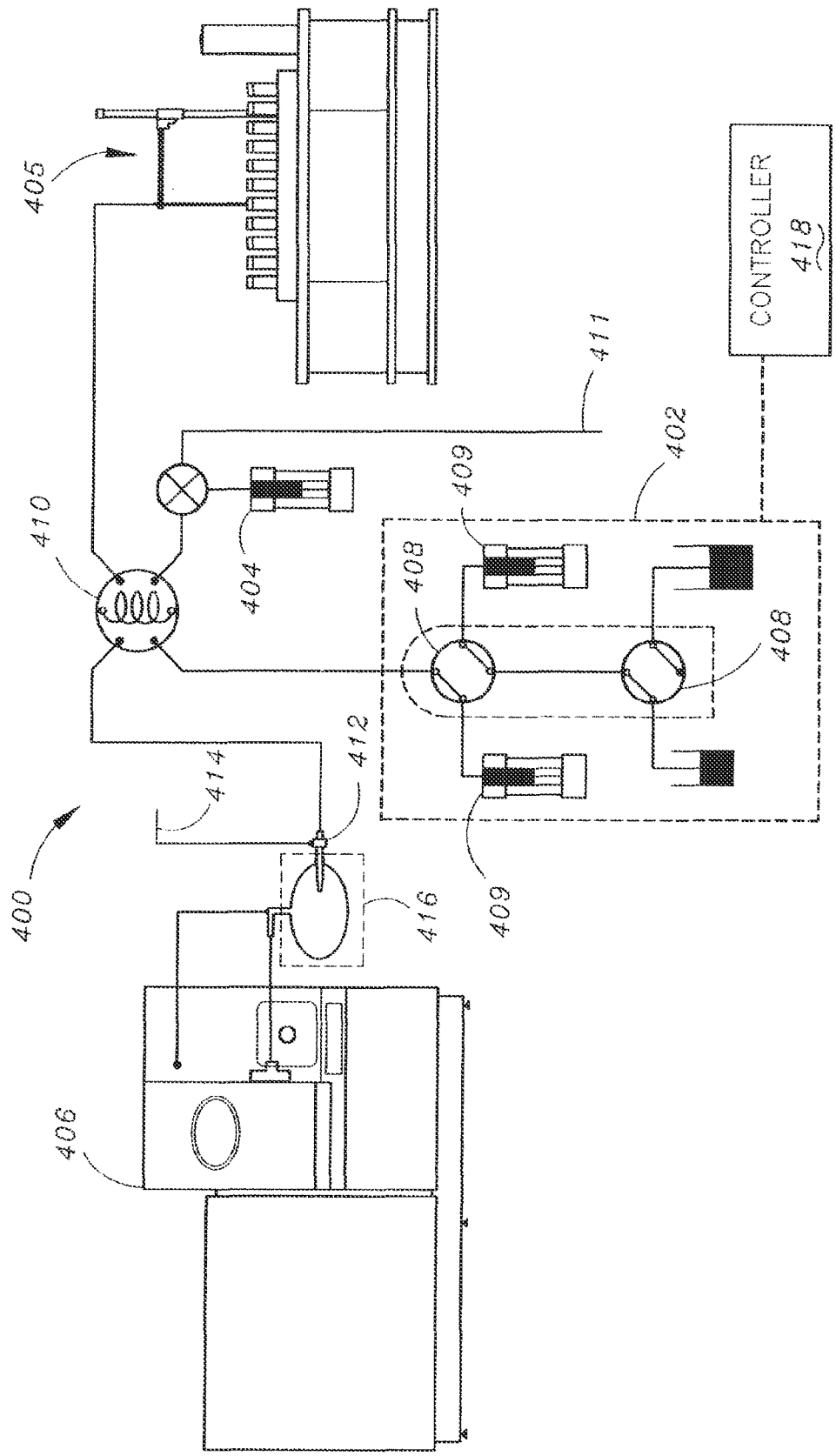
FIG. 18 is a schematic illustration of a sample analysis system according to another exemplary embodiment of the present disclosure.

Referring now to FIG. 18, a schematic illustration of a sample analysis system 400 is shown according to another exemplary embodiment of the present disclosure. The sample analysis system 400 includes a continuous flow pump 402, a sample pump 404, and an analytical device 406. The continuous flow pump 402 may function similarly to the continuous flow pump 100 as described above with reference to FIGS. 1-8. For instance, at least two syringes may be alternately loaded and dispensed via two valves to continuously output fluid without substantial addition of gas, while maintaining a clean and low flow rate of fluid. While the continuous flow pump 402 is shown in FIG. 18 with two 4-port valves 408 and two syringes 409, it may be appreciated that other suitable valve and syringe configurations may be utilized. The sample pump 404 may be configured to introduce a sample solution to the sample analysis system 400. For example, a sample may be drawn from an auto sampler 405, and introduced into the sample analysis system 400 by the sample pump 404, such as by forming a sample solution from solution contained in the sample pump 404. The analytical device 406 may be configured to analyze the composition of the sample solution. For instance, the analytical device 406 may be an inductively coupled plasma mass spectrometry (ICP-MS) spectrometer, or other device sufficient to analyze the composition of the sample solution.

The sample analysis system 400 may also include a system valve 410. The system valve 408 may be configured to couple between each of the continuous flow pump 402, the sample pump 404, and the analytical device 406. The system valve 408 may be operable to selectively permit fluid flow between the continuous flow pump 402, the sample pump 404, the auto sampler 405, and the analytical device 406. The sample analysis system 400 may include lines with matched restriction. The lines may include those within the continuous flow pump 402 and the line leading from the continuous flow pump 402 to the system valve 408. For instance, a matched restriction may indicate one or more of a matching line diameter, low pressurization, and substantially no pressurization. The sample analysis system 400 may also include a waste line 411.

The sample analysis system 400 may further include a nebulizer 412. The nebulizer 412 may include a gaseous feed source 414 to assist in atomizing the fluid fed into the nebulizer 412. For example, the gaseous feed source 414 may feed argon into the nebulizer at a constant feed rate. However, it may be appreciated that a variety of gases and mixtures of gases may be provided to the nebulizer 412 depending on the fluids to be tested by the analytical device 406. The nebulizer 412 may also be coupled with a spray chamber 416. The spray chamber 416 may further prepare the sample to be tested in the analytical device 406, such as by filtering the sample mist to permit an appropriate droplet size distribution to feed into the analytical device 406. Additionally, the spray chamber 416 may be cooled, such as via a peltier device or a low temperature peltier device. For instance, the spray chamber 416 may be a high-efficiency cyclonic spray chamber coupled with a peltier device.

The sample analysis system 400 may additionally include a controller 418 configured to control the operation of the continuous flow pump 402. The controller 418 may operate substantially similar to the controller 122 of the continuous flow pump 100 and/or to the controller 222 of the continuous flow pump 200, as shown in FIGS. 1 and 9, respectively, and described above.

It is believed that the present disclosure and many of its attendant advantages will be understood by the foregoing description, and it will be apparent that various changes may be made in the form, construction and arrangement of the components thereof without departing from the scope and spirit of the disclosure or without sacrificing all of its material advantages. The form herein before described being merely an explanatory embodiment thereof, it is the intention of the following claims to encompass and include such changes.

What is claimed is:

1. A continuous flow syringe pump, comprising:
   a first syringe configured for at least one of loading or dispensing at least one fluid;
   a second syringe configured for at least one of loading or dispensing the at least one fluid;
   a first valve connected to the first syringe and the second syringe, the first valve including at least four ports into or out of which fluid may pass, the first valve configured for providing fluid to or receiving fluid from each of the first syringe and the second syringe;
   a second valve connected to the first valve, the second valve including at least four ports into or out of which fluid may pass;
   at least one fluid source connected to the second valve, the first syringe and the second syringe configured to independently draw the at least one fluid from the at least one fluid source through the second valve and the first valve; and
   at least one outlet connected to the first valve, the at least one outlet configured to alternate output of the at least one fluid between the first syringe and the second syringe in a substantially continuous operation.

2. The continuous flow syringe pump of claim 1, wherein the at least one fluid is at least one of a carrier solution or an internal standard solution.

3. The continuous flow syringe pump of claim 1, further including: a container connected to the second valve, the container configured for receiving fluid from the first syringe and the second syringe.

4. The continuous flow syringe pump of claim 1, wherein the first valve includes two tube segments, each of the two tube segments configured to connect to two ports of the first valve.

5. The continuous flow syringe pump of claim 4, wherein each of the two tube segments connect two adjacent ports.

6. The continuous flow syringe pump of claim 1, wherein the second valve includes a port-blocking device, the port-blocking device configured to block one of the at least four ports of the second valve.

7. The continuous flow syringe pump of claim 1, wherein the first valve is configured for providing fluid to or receiving fluid from each of the first syringe and the second syringe simultaneously.

8. The continuous flow syringe pump of claim 1, further including: a controller, the controller configured to control operation of at least one of the first valve, the second valve, the first syringe, or the second syringe.

9. A continuous flow pump, comprising:
   a first syringe device configured for at least one of loading or dispensing at least two fluids, the first syringe device including a first syringe and a second syringe;
   a second syringe device configured for at least one of loading or dispensing the at least two fluids, the second syringe device including a third syringe and a fourth syringe;
   a first valve connected to the first syringe device and the second syringe device, the first valve including at least eight ports into or out of which fluid may pass, the first valve configured for providing fluid to or receiving fluid from each of the first syringe, the second syringe, the third syringe, and the fourth syringe;
   a second valve connected to the first valve, the second valve including at least four ports into or out of which fluid may pass; and
   at least two outlets connected to the first valve, each of the at least two outlet configured to alternate output of the at least two fluids between the first syringe device and the second syringe device in a substantially continuous operation.

10. The continuous flow pump of claim 9, wherein the at least two fluids include at least one of a carrier solution or an internal standard solution.

11. The continuous flow pump of claim 9, further including:
    a first container connected to the second valve, the first container configured for receiving one of the at least two fluids from the first syringe device and the second syringe device; and
    a second container connected to the second valve, the second contained configured for receiving another of the at least two fluids from the first syringe device and the second syringe device.

12. The continuous flow pump of claim 9, wherein the first valve includes at least four tube segments, each of the at least four tube segments configured to connect to two ports of the first valve.

13. The continuous flow pump of claim 12, wherein each of the at least four tube segments connect two adjacent ports.

14. The continuous flow pump of claim 9, further including:
    at least two fluid sources connected to the second valve, the first syringe device and the second syringe device configured to independently draw the at least two fluids from the at least two fluid sources through the second valve and the first valve.

15. The continuous flow pump of claim 9, wherein the first valve is configured for providing fluid to or receiving fluid from each of the first syringe, the second syringe, the third syringe, and the fourth syringe simultaneously.

16. The continuous flow pump of claim 9, further including:
    a controller, the controller configured to control operation of at least one of the first valve, the second valve, the first syringe device, or the second syringe device.

17. A sample analysis system, comprising:
    a continuous flow pump, the continuous flow pump including:
       a first syringe configured for at least one of loading or dispensing at least one fluid;
       a second syringe configured for at least one of loading or dispensing the at least one fluid;
       a first valve connected to the first syringe and the second syringe, the first valve including at least four ports into or out of which fluid may pass, the first valve configured for providing fluid to or receiving fluid from each of the first syringe and the second syringe simultaneously;

a second valve connected to the first valve, the second valve including at least four ports into or out of which fluid may pass; and at least one outlet connected to the first valve, the at least one outlet configured to alternate output of the at least one fluid between the first syringe and the second syringe in a substantially continuous operation;

a sample pump, the sample pump configured to introduce a sample solution to the sample analysis system; and an analytical device, the analytical device configured to analyze the composition of at least the sample solution.

18. The sample analysis system of claim 17, further including: a system valve, the system valve coupled to each of the continuous flow pump, the sample pump, and the analytical device.

19. The sample analysis system of claim 18, further including: a nebulizer, the nebulizer coupled between the analytical device and the system valve.

* * * * *